United States Patent [19]

Lord

[11] 4,206,545
[45] Jun. 10, 1980

[54] PREFABRICATED FULL CROWN SYSTEM

[76] Inventor: Raymond E. Lord, 418 Church St., North Adams, Mass. 01247

[21] Appl. No.: 888,180

[22] Filed: Mar. 20, 1978

[51] Int. Cl.² .................................................. A61C 5/08
[52] U.S. Cl. ..................................... 433/183; 433/222
[58] Field of Search ..................................... 32/12, 6, 5

[56] References Cited

U.S. PATENT DOCUMENTS

| | | | |
|---|---|---|---|
| 2,930,125 | 3/1960 | Pos | 32/12 |
| 3,058,216 | 10/1962 | Cohen | 32/12 |
| 3,102,337 | 9/1963 | Mintz | 32/12 |
| 3,375,582 | 4/1968 | Myerson | 32/12 |

FOREIGN PATENT DOCUMENTS

| | | | |
|---|---|---|---|
| 874058 | 7/1949 | Fed. Rep. of Germany | 32/12 |
| 776119 | 7/1935 | France | 32/12 |

*Primary Examiner*—Russell R. Kinsey
*Assistant Examiner*—John J. Wilson

[57] ABSTRACT

Two preformed pieces are joined onto a natural tooth to constitute a single thickness crown offering the esthetics of a facing and the utility of a full metal cap. Splinting of a dummy tooth between two of the crown assemblies is also accomplished at chairside in conjunction with a routine office-lab procedure.

5 Claims, 5 Drawing Figures

PREFABRICATED FULL CROWN SYSTEM

BACKGROUND OF THE INVENTION

This invention relates to a full crown system, and more particularly to such a system permitting both direct or indirect construction of the crown.

Prior art full crowns have been constructed in accordance with several accepted systems either for direct or for indirect placement of the crown. Direct placement involves only procedures that may be performed at chairside. Indirect placement involves procedures that require laboratory work in addition to chairside work.

Full crowns have been constructed in the prior art solely of esthetic materials such as porcelain, various plastics, and composite materials. The most successful method has been to cast a crown and follow with an esthetic facing over the casting.

Attempts have also been made in the prior art to form a metal crown and follow with an esthetic window. The opposite, forming an esthetic crown and adding a metal at points of stress, has also been employed. Neither system successfully satisfies esthetics and function simultaneously.

SUMMARY OF THE INVENTION

It is an object of this invention to provide a full crown system for application of a combination crown at chairside during a single visit. Another object is to provide a full crown system that facilitates the splinting of multiple teeth. The crowns of this invention are not limited to particular teeth in the dental arch, but rather are usable in the restoration of all teeth.

In accordance with this invention a full crown system employs two separate pieces each having a function and joined at chairside to provide a single thickness crown having the esthetics of a facing and the utilization strength of a full crown.

DESCRIPTION OF THE PREFERRED EMBODIMENTS

In general, the full crown system of this invention provides a full coverage of a tooth with a single thickness crown by joining two partial crown members to restore both function and esthetics of the tooth. The functional member is made of metal, and the esthetic member of plastic or other esthetic material.

This crown system combines the strength of preformed metal on four surfaces (mesial, distal, lingual, and occlusal or incisal) with the esthetic or facial (labial) surface being of a plastic material. Both members are preformed and can be joined into a single thickness crown at chairside. Splinting to provide a replacement tooth or to stabilize the dental arch is attained by a soldering or welding procedure which bridges across to the metal members of adjacent crowns of this invention.

The full crown system of this invention satisfies function and esthetics with two independent entities combined to form one functional and esthetic unit. There is no known combination that can be performed by a practicing dentist at chairside that will totally satisfy both function and esthetics by the combination of metal and esthetic units.

In addition, there is no known combination that permits splinting as a simplified, inexpensive procedure. Such splinting, meaning to include the replacement of a missing tooth by the inclusion of a "dummy" tooth herein described.

Further, this crown system can be adapted to other prosthetic systems. The metallic portion of the crown can be specially preformed to receive routine or precision clasping procedures for partial dentures.

Practice of this system requires the provision of the usual range of sizes and shapes of both crown members, and the usual shades of the facial or esthetic crown member to meet the normal variations encountered in restoring coronal areas. Thereafter the metal backing member and the esthetic facing member are connected, filled with a plastic mix and fitted to the prepared natural tooth and cemented directly to the tooth. While it is a feature of this invention that all work required to accomplish the crown can be performed chairside, the crown members of this system are so constructed and arranged as to permit simple laboratory procedures when found necessary.

The lingual, incisal or occlusal and proximal surfaces of this crown system are composed of a metal preferably stainless steel of approximately ten mils thickness. Only the facial surface of this crown system is composed of esthetic material, preferably 10 mil acrylic plastic.

Figure 1:
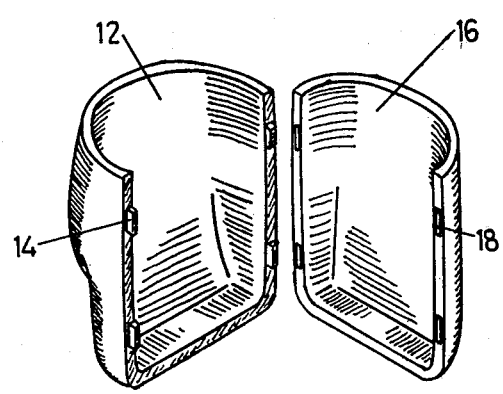
FIG. 1 is an exploded perspective of the two pieces of the crown for an anterior tooth.
Figure 2:
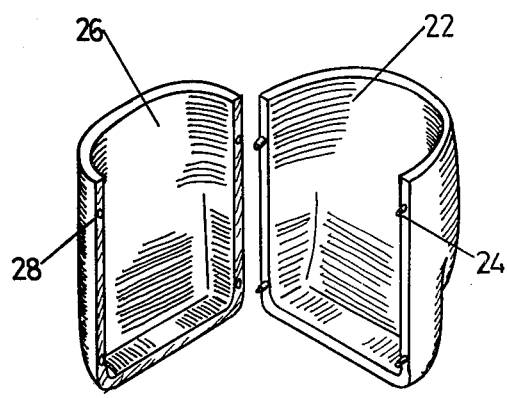
FIG. 2 is an exploded view of another embodiment of the crown for an anterior tooth.
Figure 3:
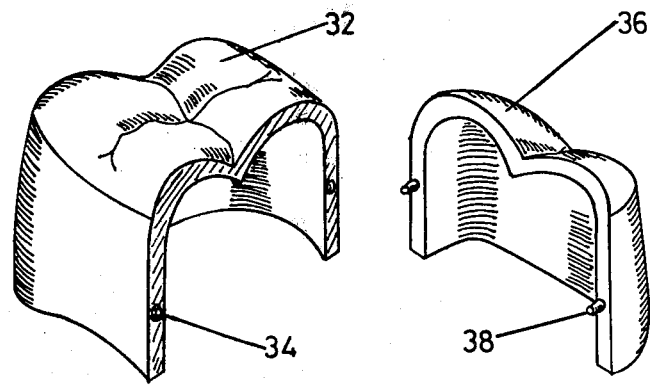
FIG. 3 is an exploded perspective of the two pieces of the crown for a posterior tooth.

FIGS. 1, 2 and 3 show backing crown members 12, 22 and 32 which provide metal surfaces for all of the functional surfaces of anterior and posterior teeth, respectively. Conversely only the esthetic facial surfaces of the crown 16, 26 and 36, respectively, are composed of the plastic material. The metal backing members are provided with male mating members 14, 24 and 38, respectively, while corresponding female members 18, 28 and 34 are provided on the plastic facing members.

The backing and facing can be correctly oriented by the male members of the facing inserted into the female members of the backing.

The two separate parts become one unit with the addition of a plastic mix or fill which engages the flange and hardens. (The addition of spars, partial or complete, increases the mechanical retention.)

This assembly is applicable to both anterior and posterior teeth.

The natural tooth of the patient is prepared for the crowns of this invention according to procedures for full crowns which are well-known to the art, and no additional or different procedures need be learned by the practitioner. Properly prepared anterior teeth are shown at 42 and 46 in FIG. 4. The correct size and shape of the backing and facing crown members needed for the prepared tooth are established by observation and/or measurement. The cervical (gingival) border of the crown members is trimmed to adapt to the prepared tooth. Then a conventional plastic mix or fill, with a catalyst to provide controlled hardening, is placed in the crown and the crown is fitted to the prepared tooth.

The fill also serves with the mating members to secure the metal backing crown member to the plastic facing member. Excess fill material which is extruded from the crown during the fitting procedure is trimmed away and the margins are defined. The crown is then cemented in place in accordance with standard operating procedures.

Indirect or laboratory assembly of this crown system may be practiced where deemed advisable by utilizing a model of the patients' tooth/teeth in the fully prepared stage. The prefabricated crown is luted to the model with a conventional wax. The assembly is flasked, as for a facing or denture type of operation. The flask is separated after hardening to expose the interior of the prefabricated veneer crown. The crown is then filled to excess with the fill or mix, as in the direct chairside method described above, and the flask is closed to allow the fill to cure. Thereafter the flask is opened, the crown removed and trimmed, and the crown is cemented to the prepared tooth.

Figure 4:
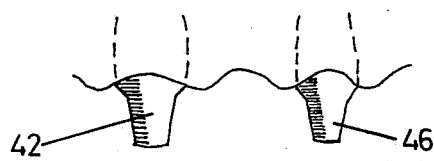
FIG. 4 is an elevation of a lingual view of prepared teeth flanking a missing tooth.
Figure 5:
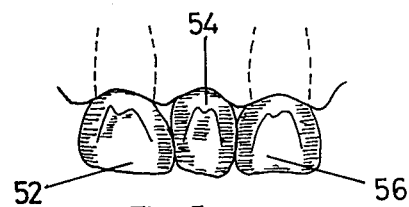
FIG. 5 is the elevation showing the splinting of a pontic or dummy tooth between crowns of this invention on the prepared teeth of FIG. 4.

Splinting of prefabricated esthetic crowns of this invention is shown in FIGS. 4 and 5 for a missing anterior tooth. It should be understood that the procedures for splinting posterior teeth are essentially the same as described hereinafter for the anterior teeth. Two or more prefabricated crowns 52 and 56 of this invention are provided for prepared teeth 42 and 46. The crowns, including a dummy tooth 54, are fitted to the patient and the facings are luted with a suitable wax.

An impression is made with a rigid material such as French's plaster to cover the lingual surface in the anterior area and the lingual and occlusal in posterior area. The facings are removed from the backings. To the exposed interior surface of the backings is poured a refractory material. When the refractory material is hard, the original plaster-type impression material is removed. This leaves the backings accurately related and held by the hardened refractory material. The backings are combined by a suitable solder and then broken free of the refractory material. The facings are replaced in their correct positions. The fill is placed on the interior of the prefabricated veneer crowns and the direct placement procedure is followed. The foregoing may be accomplished with a model of the prepared teeth in relation to each other as in the indirect assembly technique.

What is claimed is:

1. A full crown system comprising a single thickness crown of two separate pieces joined to form a unitary crown adapted to be mounted on and surround a prepared tooth stump to be capped, each of said pieces extending only part way around said stump when mounted thereon, one of said pieces being a metal member providing all of the mesial, distal, lingual, and occlusal or incisal surfaces of the crown, the other of said pieces being a plastic member providing only the esthetic facial surface of the crown, mating surfaces provided on said two pieces serving to join or splint said members without overlap of said members.

2. The full crown system of claim 1 wherein a pair of said single thickness crowns is splinted to an intervening pontic member to effect replacement of a missing tooth.

3. The full crown system of claim 2 wherein said pontic is joined to said metal member of each of said pair of crowns.

4. The full crown system of claim 1 wherein said metal member is formed to permit precision clasping for partial denture construction.

5. The full crown system of claim 1 wherein said metal member is 10 mil stainless steel, and said plastic member is 10 mil acrylic plastic.

* * * * *